United States Patent
Ahn et al.

(10) Patent No.: US 10,015,841 B2
(45) Date of Patent: Jul. 3, 2018

(54) MICRO HEATER AND MICRO SENSOR AND MANUFACTURING METHODS THEREOF

(71) Applicant: Point Engineering Co., Ltd., Asan-si (KR)

(72) Inventors: Bum Mo Ahn, Suwon-si (KR); Seung Ho Park, Hwaseong-si (KR); Sung Hyun Byun, Hwaseong-si (KR)

(73) Assignee: Point Engineering Co., Ltd., Asan-si, Chungcheongnam-do (KR)

( * ) Notice: Subject to any disclaimer, the term of this patent is extended or adjusted under 35 U.S.C. 154(b) by 210 days.

(21) Appl. No.: 14/864,184

(22) Filed: Sep. 24, 2015

(65) Prior Publication Data

US 2016/0084787 A1    Mar. 24, 2016

(30) Foreign Application Priority Data

Sep. 24, 2014  (KR) .................. 10-2014-0127619
Sep. 24, 2014  (KR) .................. 10-2014-0127620

(51) Int. Cl.
*G01N 27/12* (2006.01)
*H05B 3/03* (2006.01)
*H05B 3/26* (2006.01)

(52) U.S. Cl.
CPC ............... *H05B 3/03* (2013.01); *H05B 3/262* (2013.01); *G01N 27/12* (2013.01); *H05B 2203/014* (2013.01); *H05B 2203/017* (2013.01)

(58) Field of Classification Search
CPC .... G01N 27/12; G01N 27/227; G01N 27/128; G01N 27/123; G01N 33/0027; H05B 3/03; H05B 3/262; H05B 2203/014; H05B 2203/017
See application file for complete search history.

(56) References Cited

U.S. PATENT DOCUMENTS

| | | |
|---|---|---|
| 5,464,966 A | 11/1995 | Gaitan et al. |
| 5,756,971 A | 5/1998 | Hipp |
| 5,821,402 A * | 10/1998 | Okajima ................. C23C 16/04 422/90 |
| 7,861,575 B2 | 1/2011 | Jun et al. ...................... 73/31.06 |
| 8,325,460 B2 | 12/2012 | Park et al. ..................... 361/286 |
| 8,354,729 B2 * | 1/2013 | Hsieh ................... G01N 27/128 257/414 |
| 2002/0118027 A1 | 8/2002 | Routkevitch et al. ........ 324/694 |
| 2004/0195096 A1* | 10/2004 | Tsamis ................ B81C 1/00682 204/426 |
| 2004/0213702 A1 | 10/2004 | Ingrisch |
| 2007/0062812 A1 | 3/2007 | Weber et al. |
| 2008/0134753 A1 | 6/2008 | Jun et al. |
| 2009/0151429 A1 | 6/2009 | Jun et al. |
| 2010/0134948 A1 | 6/2010 | Park et al. ..................... 361/286 |

(Continued)

FOREIGN PATENT DOCUMENTS

| | | | | |
|---|---|---|---|---|
| AT | 508 976 A1 | 5/2011 | ............. | G01N 27/12 |
| EP | 2 533 037 A1 | 12/2012 | ............. | G01N 27/12 |

(Continued)

*Primary Examiner* — Blake A Tankersley
(74) *Attorney, Agent, or Firm* — Sunstein Kann Murphy & Timbers LLP

(57) ABSTRACT

A micro heater and a micro sensor is capable of providing a heater having a small thermal capacity by forming an air gap which surrounds the heater wire, and forming the heater wire on a porous substrate.

18 Claims, 4 Drawing Sheets

(56) References Cited

U.S. PATENT DOCUMENTS

| | | | |
|---|---|---|---|
| 2015/0021716 A1 | 1/2015 | Lee et al. | |
| 2015/0285754 A1 | 10/2015 | Park et al. | |
| 2016/0370336 A1 | 12/2016 | Ahn et al. | .......... G01N 33/0027 |

FOREIGN PATENT DOCUMENTS

| | | | | |
|---|---|---|---|---|
| JP | 2006-153512 | 6/2006 | ............ | G01N 27/22 |
| JP | 2011-149889 A | 8/2011 | | |
| JP | 2012-68069 A | 4/2012 | | |
| JP | 2012-98232 A | 5/2012 | | |
| KR | 10-2009-0061864 | 6/2009 | ............... | G01N 1/22 |
| KR | 2009-0064693 | 6/2009 | ............... | B81C 1/00 |
| KR | 10-2010-0054526 | 5/2010 | ............. | G01N 27/12 |
| KR | 10-1019576 | 3/2011 | ............. | G01N 27/12 |
| KR | 10-2014-0106082 | 9/2014 | ........... | G01N 27/403 |
| KR | 10-2014-0118021 | 10/2014 | .......... | G01N 27/407 |
| KR | 10-2015-0010473 | 1/2015 | | |

\* cited by examiner

MICRO HEATER AND MICRO SENSOR AND MANUFACTURING METHODS THEREOF

CROSS-REFERENCE TO RELATED PATENT APPLICATION

This U.S. non-provisional patent application claims priority under 35 U.S.C. § 119 of Korean Patent Application Nos. 10-2014-0127619 and 10-2014-0127620 filed on Sep. 24, 2014 in the Korean Patent Office, the entire contents of which are hereby incorporated by reference.

BACKGROUND

1. Technical Field

The present invention relates to a micro heater and a micro sensor, more particularly, relates to a micro heater and a micro sensor, wherein an air gap surrounding the heater wire is formed, and the heater wire is formed on a porous substrate.

2. Description of the Related Art

As attention on the environmental issue is gradually increasing in these days, development of a small sensor which can obtain accurate and various information in a short time is required. Especially efforts on miniaturization, accuracy enhancement, and cost reduction of the gas sensors in order to measure related gas concentration easily for a comfortable living space, management of harmful industrial environment, food price, food production process management, and the like, have been progressed.

Nowadays, gas sensors are gradually evolving from the conventional structure comprising sintered ceramics or thick films to the structure comprising Micro Electro Mechanical System (MEMS) by adopting semiconductor process technology.

Reviewing from the aspects of measurement methods, currently the most widely used technique for a gas sensor is to measure the change in the electrical characteristics of the sensing material of the sensor when gas is being absorbed therein. Metal oxide such as $SnO_2$ is commonly used as a sensing material, and it is advantageous in that the measurement method is relatively simple wherein the change in the electrical conductivity is measured according to the gas concentration of the object gas. At this time, the sensing material of the metal oxide is heated to a high temperature, and the variation in the measurement values during the operation thereof becomes more significant, therefore, precise temperature control is essential for a fast and precise measurement of the gas concentration. And, when measuring, residual gases or moistures which had already been absorbed in the sensing material are being forcibly removed by heating with high temperature, and the sensing material is reset to the original state thereof, and then the gas concentration is measured. Therefore, the temperature characteristics of the gas sensor directly affect key measurement factors such as sensitivity, recovery time, response time, and the like of the sensor.

Thus, for an efficient heating, a micro heater type is effective which can heat only the sensing material locally and uniformly. However, when measuring with a micro gas sensor, if large power consumption is needed for temperature control, then a large battery or a large power source is required even though the volume of the sensor and measurement circuit is small, thus, the size of the entire measurement system will be determined by these factors eventually. Therefore, in order to implement a micro gas sensor, a structure of low power consumption must be considered in the first place.

Until this time, when manufacturing most micro gas sensors silicon substrate of a very large heat conductivity is commonly used, therefore, in order to reduce heat loss a suspended structure separated from the substrate is formed by forming an etched pit or a groove inside the sensor structure using a bulk micromachining process, and then micro heater, insulation layer, sensing material, and the like are sequentially formed on this structure, and in such a way, a portion of the heat transfer loss can be reduced. However, in this case, since the manufacturing method is based on a wet etching process utilizing the crystalline directivity of the substrate itself, there is a limitation in miniaturization of the sensor element, furthermore, there has been a problem of compatibility with the standard CMOS semiconductor process due to the physical property of the etchant being used such as potassium hydroxide (KOH) and the like.

PATENT LITERATURE

Korea Patent Publication No. 2009-0064693

SUMMARY

Embodiments of the present invention, may solve the above described problems by providing a micro heater having a small heat capacity and a micro sensor.

A micro heater embodiment of the present invention includes: a porous substrate; and a heater electrode which is formed on the porous substrate and includes a heater wire and a heater electrode pad which is connected to the heater wire, wherein an air gap which surrounds the heater wire is formed in the porous substrate.

Another micro heater embodiment of the present invention includes: a porous substrate; and a heater electrode which is formed on the porous substrate and includes a heater wire and a heater electrode pad which is connected to the heater wire, wherein a first supporting portion which supports the heater wire and a second supporting portion which supports the heater electrode pad are formed on the porous substrate, and an air gap is formed between the first supporting portion and the second supporting portion, and the shape of the second supporting portion is formed to be identical or similar to the shape of the heater electrode pad.

The porous substrate is formed of an aluminum oxide porous layer; the area of the first supporting portion is formed to have a larger area than that of the heater wire; a discoloration protection layer is formed on the upper side of the heater electrode; the discoloration protection layer comprises oxide series material; the discoloration protection layer is silicon dioxide or aluminum oxide; a soldering metal is formed in the end of the heater electrode pad; and the soldering metal may be at least one of gold, silver, and tin.

A micro sensor embodiment of the present invention includes: a porous substrate; a sensor electrode which is formed on the porous substrate and includes a sensor wire and a sensor electrode pad which is connected to the sensor wire; and a heater electrode which is formed on the porous substrate and includes a heater electrode pad and a heater wire which is connected to the heater electrode pad and disposed closer to the sensor wire than the sensor electrode pad, wherein an air gap which surrounds the heater wire and the sensor wire is formed in the porous substrate.

In the above described configuration, the porous substrate is formed with an aluminum oxide porous layer, and may further include a sensing material covering the heater wire and the sensor wire.

Another micro sensor embodiment of the present invention includes: a heater electrode which includes a heater wire wherein a plurality of first protrusions are formed in the end portion thereof, and a heater electrode pad being connected to the heater wire; a sensor electrode which includes a sensor wire wherein a plurality of second protrusions disposed between the first protrusions, and a sensor electrode pad being connected to the sensor wire; and an aluminum oxide porous layer which supports the heater electrode and the sensor electrode, wherein an air gap is formed between said heater electrode pad and said sensor electrode pad by removing a portion of said aluminum oxide porous layer.

The aluminum oxide porous layer includes a first supporting portion which supports the heater wire and the sensor wire, wherein the air gap may be formed outside of the first supporting portion.

The aluminum oxide porous layer may include: a first supporting portion which supports the heater wire and the sensor wire; a heater electrode pad support which supports the heater electrode pad and formed to have a same outline of the heater electrode pad but having a wider width than that of the heater electrode pad; and a sensor electrode pad support which supports the sensor electrode pad and formed to have a same outline of the sensor electrode pad but having a wider width than that of the sensor electrode pad.

A sensing material is additionally formed in the location corresponding to the first supporting portion; the sensing material is formed by printing; at least two of the heater electrode pads are formed; a discoloration protection layer is formed on the upper side of the heater electrode or the sensor electrode; the discoloration protection layer comprises oxide series material; the discoloration protection layer is silicon dioxide or aluminum oxide; a soldering metal is formed in the end of the heater electrode pad or the sensor electrode pad; and the soldering metal may be at least one of gold, silver, and tin.

In addition, the air gap is formed to surround the first supporting portion.

Another micro sensor embodiment of the present invention includes: a porous substrate; a sensor electrode which is formed on the porous substrate and includes a sensor wire and a sensor electrode pad which is connected to the sensor wire; and a heater electrode which is formed on the porous substrate and includes a heater wire and heater electrode pad which is connected to the heater wire, wherein the porous substrate includes: a sensor electrode pad support which supports the sensor electrode pad; and a heater electrode pad support which supports the heater electrode pad, wherein an air gap is formed between the heater electrode pad support and the sensor electrode pad support.

Yet another micro sensor embodiment of the present invention includes: a porous substrate; a sensor electrode which is formed on the porous substrate and includes a sensor wire and a sensor electrode pad which is connected to the sensor wire; a heater electrode which is formed on the porous substrate and includes a heater wire and a heater electrode pad which is connected to the heater wire, wherein the porous substrate includes: a first supporting portion which supports the heater wire and the sensor wire; a heater electrode pad support which supports the heater electrode pad; and a sensor electrode pad support which supports the sensor electrode pad, wherein an air gap is formed by removing the area except the first supporting portion, the heater electrode pad support, and the sensor electrode pad support.

Still yet another micro sensor embodiment of the present invention includes: a heater electrode which includes a heater wire wherein a plurality of first protrusions are formed in the end portion thereof, and a first and a second heater electrode pads which is connected to the both sides of the heater wire; a sensor electrode which includes a sensor wire wherein a plurality of second protrusion disposed between the first protrusions, and a sensor electrode pad which is connected to the sensor wire; and a porous substrate which supports the heater electrode and the sensor electrode, wherein the porous substrate includes: a first supporting portion supporting the heater wire and the sensor wire; a first heater electrode pad support which supports the first heater electrode pad; a second heater electrode pad support which supports the second heater electrode pad; a sensor electrode pad support which supports the sensor electrode pad; and an air gap which is formed outer side of the first supporting portion.

At least a portion of the first heater electrode pad support, the second heater electrode pad support, and the sensor electrode pad support may be separated from each other by the air gap.

A micro heater embodiment of the present invention includes: a porous substrate; and a heater electrode which is formed on the porous substrate and includes a heater wire and a heater electrode pad which is connected to the heater wire, wherein an air gap which surrounds the heater wire is formed in the porous substrate; and an opening, which is disposed in the lower portion of the heater wire and communicating with the air gap, is formed in the lower portion of the porous substrate.

The porous substrate may be formed with aluminum oxide; a plurality of pores are penetratingly formed along the vertical direction in the porous substrate; and the pores can be communicating with the opening.

A micro sensor embodiment of the present invention includes: a porous substrate; a sensor electrode which is formed on the porous substrate and includes a sensor wire, and a sensor electrode pad which is connected to the sensor wire; and a heater electrode which is formed on the porous substrate and includes a heater electrode pad, and a heater wire which is connected to the heater electrode pad and disposed closer to the sensor wire than the sensor electrode pad, wherein an air gap, which surrounds the heater wire and the sensor wire, is formed in the porous substrate; and an opening, which is disposed in the lower portion of the heater wire and communicating with the air gap, is formed in the lower portion of the porous substrate.

A sensing material may be formed in the porous substrate in a way that the heater wire and the sensor wire are covered thereby.

A method for manufacturing a micro heater in accordance with an embodiment of the present invention includes the steps of: forming a heater electrode in the porous substrate wherein an opening is formed in the lower portion thereof; and forming an air gap in the porous substrate, wherein the air gap is communicating with the opening and formed to surround the heater wire of the heater electrode.

The step of forming an air gap may include the steps of: forming a cover layer, wherein an engraved air gap pattern corresponds to the area wherein the air gap is formed, in the porous substrate and the heater electrode; and etching the exposed area with the engraved air gap pattern in the porous substrate, wherein the step of forming the porous substrate may include the steps of: forming aluminum oxide porous layer through the oxidation of the aluminum substrate; forming a mask on the aluminum oxide porous layer; thickening the aluminum oxide porous layer in the aluminum substrate through the oxidation of the area except the mask; and removing the mask and forming an opening through the etching of the area except the aluminum oxide porous layer in the aluminum substrate.

A method for manufacturing a micro sensor in accordance with an embodiment of the present invention includes the steps of: forming a heater electrode and a sensor electrode in the porous substrate wherein an opening is formed in the lower portion thereof; and forming an air gap in the porous substrate, wherein the air gap is communicating with the opening and formed to surround the heater wire of the heater electrode and the sensor wire of the sensor electrode.

After the step of forming an air gap, a step of forming a sensing material in the porous substrate may further be included so as to cover the heater wire and the sensor wire.

Another micro sensor embodiment of the present invention includes: a heater electrode which includes a heater wire wherein a plurality of first protrusions are formed in the end portion thereof, and a heater electrode pad being connected to the heater wire; a sensor electrode which includes a sensor wire wherein a plurality of second protrusions disposed between the first protrusions, and a sensor electrode pad being connected to the sensor wire; and an aluminum oxide porous layer which supports the heater electrode and the sensor electrode, wherein an air gap is formed by removing a portion of the aluminum oxide porous layer so as to surround the heater wire and the sensor wire; and an opening, disposed in the lower portion of the heater wire and the sensor wire and communicating with the air gap, is formed in the lower portion of the aluminum oxide porous layer.

The aluminum oxide porous layer includes a first supporting portion which supports the heater wire and the sensor wire, wherein the air gap is formed outside of the first supporting portion; a sensing material is additionally formed in the location corresponding to the first supporting portion; at least two of the heater electrode pads are formed; a plurality of pores are penetratingly formed along the vertical direction in the porous substrate; and the pores can be communicating with the opening.

DETAILED DESCRIPTION OF EMBODIMENTS

Hereinafter, a preferred exemplary embodiment of the present invention will be described in detail with reference to the accompanying drawings.

Example 1

Figure 1:
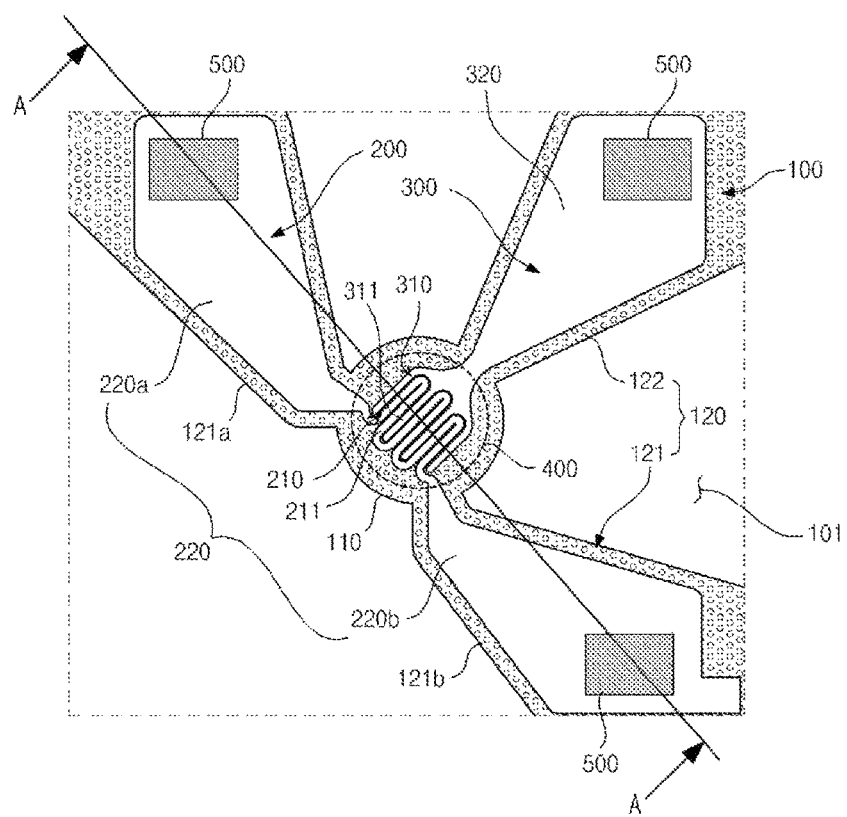
FIG. 1 is a plan view of a micro sensor provided with a micro heater according to Example 1 of the present invention.
Figure 2:
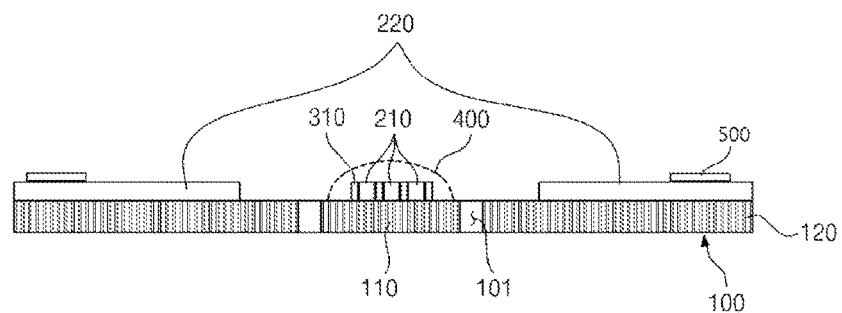
FIG. 2 is a cross-sectional view of FIG. 1 along the line A-A.

A micro sensor provided with a micro heater of Example 1, as illustrated in FIGS. 1 and 2, includes: a porous substrate 100; a sensor electrode 300 which is formed on the porous substrate 100 and includes a sensor wire 310 and a sensor electrode pad 320 which is connected to the sensor wire 310; and a heater electrode 200 which is formed on the porous substrate 100 and includes a heater electrode pad 220 and a heater wire 210 which is connected to the heater electrode pad 220 and disposed closer to the sensor wire 310 than the sensor electrode pad 320, wherein the heater wire 210 and the sensor wire 310 are formed on the porous layer formed on the porous substrate 100; and an air gap 101 which surrounds the heater wire 210 and the sensor wire 310 is formed in the porous substrate 100.

The porous substrate 100 is formed with an aluminum material, and formed into a rectangular plate like shape.

The porous substrate 100 is formed with a porous layer. That is, the porous substrate 100 is formed with a porous material. Thus, a plurality of holes with open upper ends are formed along the vertical direction in the porous substrate 100. Unlike the above description, the porous substrate may be partially formed, for example, in the upper portion of the porous substrate 100.

The porous substrate 100 can be formed through the oxidation of an aluminum substrate. Therefore, the porous substrate is an anodic aluminum oxide (AAO).

The sensor electrode 300 is formed on the upper surface of the porous substrate 100.

Such sensor electrode 300 detects gases or humidity and the like.

The sensor electrode 300 includes a sensor wire 310 and a sensor electrode pad 320 which is connected to the sensor wire 310.

The sensor wire 310 is disposed in the central portion of the porous substrate 100.

A plurality of second protrusions 311 are formed at one side end of the sensor wire 310. A plurality of second grooves are formed between the second protrusions 311 and the second protrusions 311 (that is, in between the second protrusions). The second protrusions 311 disposed in the outer side are formed to have a shorter length than that of the ones disposed in the inner side.

The sensor electrode pad 320 is formed to have a wider width than that of the sensor wire 310. In addition, the sensor electrode pad 320 has a wider area than the sensor wire 310 when viewed from the top (in the plan view).

The sensor electrode pad 320 is disposed along the radial direction, and the width thereof is getting wider as it travels towards the outside. In other words, the sensor electrode pad 320 is formed in a way that the width thereof is getting narrower as it travels towards the sensor wire 310. In addition, specifically, the sensor pad 320 is disposed close to the first diagonal line of the porous substrate 100.

In addition, the sensor wire 310 is formed in a way that the width thereof is getting narrower as it travels towards the sensor electrode pad 320 (the other side of the sensor wire 310).

The heater electrode 200 is formed on the upper surface of the porous substrate 100. In this way, the thermal insulation effect is enhanced due to the pores (air holes) since the heater electrode 200 is formed on the porous layer.

The heater electrode 200 includes a heater electrode pad 220 and a heater wire 210 which is connected to the heater electrode pad 220 and disposed closer to the sensor wire 310 than the sensor electrode pad 320.

The heater wire 210 is disposed in the central portion of the porous substrate 100. In the end portion of the heater wire 210, a plurality of the first protrusions 211 which are disposed inside the second groove, and a plurality of first grooves which is disposed inside the second protrusions 311 are formed. That is, the second protrusions 311 are disposed between the first protrusions 211. The first protrusions 211 and the first grooves are plurally formed and alternately disposed. The first protrusions 211 and the first grooves are provided by the curvedly formed heater wire 210. Due to this configuration, the sensing material 400, which will be described hereinafter, can be effectively heated.

The heater electrode pad 220 is connected to both ends of the heat wire 210. In this way, at least two each of the heater electrode pad 220 are formed.

The heater electrode pad 220 is disposed close to the second diagonal line of the porous substrate 100.

The heater electrode pad 220 is disposed along the radial direction, and the width thereof is getting wider as it travels towards the outside. In other words, the sensor electrode pad 220 is formed in a way that the width thereof is getting narrower as it travels towards the heater wire 210.

The heater electrode pad 220 is formed to have a wider width than that of the heater wire 210. In addition, the heater electrode pad 220 has a larger area than that of the heater wire 210 when viewed from the top (in the plan view).

A discoloration protection layer (not shown) is formed in the entire upper portion of the heater electrode 200 and the sensor electrode 300.

The discoloration protection layer may be formed of an oxide series material.

Further, the discoloration protection layer may be silicon dioxide or aluminum oxide.

In addition, a soldering metal 500 is formed in the ends of the heater electrode pad 220 and the sensor electrode pad 320.

The soldering metal 500 is formed in the upper portion of the discoloration protection layer.

The soldering metal 500 may be at least one of gold, silver, and tin.

The air gap 101 is formed to surround the heater wire 210 and the sensor wire 310 along the circumference thereof in the porous substrate 100 of the porous substrate 100.

Unlike the one illustrated in FIG. 1, the air gap 101 is formed in an arc shape, and more than two of them can be formed along the circumferential direction or the radial direction.

The air gap 101 is penetratingly formed along the vertical direction. Unlike this, the air gap 101 may be formed in a groove shape. The width of the air gap 101 is formed to be wider than that of the first protrusion 211 or the second protrusion 311.

Figure 3:
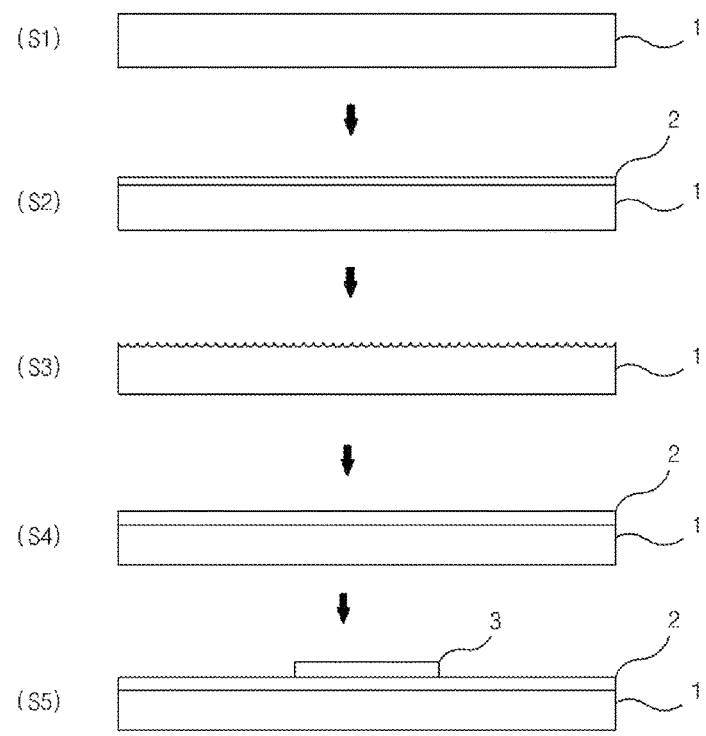
FIGS. 3 and 4 illustrate a method for manufacturing a micro sensor provided with a micro heater according to Example 2 of the present invention.

Due to the air gap 101, a first supporting portion 110 which supports the heater wire 210 and the sensor wire 310; and a second supporting portion 120 which supports the heater electrode pad 220 and the sensor electrode pad 320 are formed. That is, the air gap 101 is formed between the first supporting portion 110 and the second supporting portion 120. As illustrated in FIG. 3, the peak temperature of the radiating heat is getting higher as the width of the air gap 101 is getting wider.

The first supporting portion 110 is formed to be a circular shape which is similar to the heater wire 210 and the sensor wire 310; the first supporting portion 110 and the second supporting portion 120 are connected to each other at the area where the wires and pads are connected together; and the other portions are separated from each other due to the air gap 101. Thus, the first supporting portion 110 and the second supporting portion 120 are connected at three points.

The first supporting portion 110 is formed to be a circular shape and surrounded by the air gap 101.

The first supporting portion 110 is formed to have a larger area than that of the heater wire 210 and the sensor wire 310.

The air gap 101 is formed to be a shape which surrounds the first supporting portion 110.

Air is disposed inside the air gap 101, so that the thermal insulation effect is enhanced, the thermal conductivity is decreased, and the thermal capacity can be reduced.

Further, a sensing material 400 covering the heater wire 210 and the sensor wire 310 is formed in the first supporting portion 110.

That is, the sensing material 400 is formed at the location corresponding to the first supporting portion 110.

When the sensing material 400 is formed by printing, an imprint having the shape of a mesh network is left on the surface of the sensing material 400.

Hereinafter, the operation of Example 1 having the above described configuration will be explained.

In order to measure the gas concentration, first, a constant power is applied to the two heater electrode pads 220 of the heater electrode 200, and the area of the sensing material 400 of the center area of the sensor which is in contact therewith is heated to a constant temperature.

In this state, the change in the characteristics of the sensing material 400 generated when it is absorbed in or desorbed from the sensing material 400 corresponding to the concentration of the gas presented there around is measured using an external circuit by measuring the potential difference between the sensor electrode pads 320 which are electrically connected to the sensing material 400, and quantifying the electrical conductivity of the sensing material 400.

In addition, for a more accurate measurement, concentration of an interested gas is measured after restoring the sensing material 400 to the initial state by forcibly removing the other residual gas or moisture already absorbed in the sensing material 400 through the heating thereof to a high temperature using the heater electrode 200.

A micro sensor provided with a micro heater of another exemplary embodiment includes: a heater electrode 200 which includes a heater wire 210 wherein a plurality of first protrusions 211 are formed in the end portion thereof, and a heater electrode pad 220 being connected to the heater wire 210; a sensor electrode 300 which includes the sensor wire formed with a plurality of second protrusions 311 disposed between the first protrusions 211, and a sensor electrode pad 320 connected to the sensor wire 310; and an aluminum oxide porous layer 100 which supports the heater electrode 200 and the sensor electrode 300, wherein an air gap 101 is formed between the heater electrode pad 210 and the sensor electrode pad 310 by removing a portion of the aluminum oxide porous layer 100.

A separate detailed description will be omitted for the same elements described in the above described exemplary embodiment.

An aluminum oxide porous layer 100 includes: a first supporting portion 110 which is circularly shaped and supports the heater wire 210 and the sensor wire 310; a heater electrode pad support 121 supporting the heater electrode pad 220, and formed in the shape of the heater electrode pad 220, and having a larger width than that of the heater electrode pad 220; and a second supporting portion 120 supporting the sensor electrode pad 320, and formed in the shape of the sensor electrode pad 320, and including a sensor electrode pad support 122 having a larger width than that of the sensor electrode pad 320.

Thus, the distance between the each end (edge) of the surface of the second supporting portion 120 and the corresponding end (edge) of the surfaces of the heater electrode pad 220 and the sensor electrode pad 320 are equally maintained.

Unlike this, the first supporting portion 110 and the second supporting portion 120 may be formed to be the shape similar to the heater wire 210 and the sensor wire 310, and the heater electrode pad 220 and the sensor electrode pad 320.

The rectangular shaped aluminum oxide porous layer 100 is removed except the first supporting portion 110, the heater electrode pad support 121, and the sensor electrode pad support 122; and in this removed area (portion), an air gap 101 is formed.

The air gap 101 is formed between the heater electrode pad support 121 and the sensor electrode pad support 122.

The air gap 101 is formed outside of the first supporting portion 110.

Thus, the air gap 101 is more largely formed than the above described exemplary embodiment.

The area of the air gap 101 could be larger than the sum of the areas of the heater electrode pad 220 and the sensor electrode pad 320.

Since the aluminum oxide porous layer 100 is formed in this way, the thermal capacity can be more reduced.

A micro sensor according to another exemplary embodiment includes: a porous substrate 100; a sensor electrode 300 which is formed on the porous substrate 100 and includes a sensor wire 310 and a sensor electrode pad 320 being connected to the sensor wire 310; and a heater electrode 200 which is formed on the porous substrate 100 and includes a heater wire 210 and a heater electrode pad 220 being connected to the heater wire 210, wherein the porous substrate 100 includes: a sensor electrode pad support 122 which supports the sensor electrode pad 320; and a heater electrode pad support 121 which supports the heater electrode pad 220, wherein the air gap 101 is formed between the heater electrode pad support 121 and the sensor electrode pad support 122.

A micro sensor according to another exemplary embodiment includes: a porous substrate 100; a sensor electrode 300 which is formed on the porous substrate 100 and includes a sensor wire 310 and a sensor electrode pad 320 being connected to the sensor wire 310; and a heater electrode 200 which is formed on the porous substrate 100 and includes a heater wire 210 and a heater electrode pad 220 being connected to the heater wire 210, wherein the porous substrate 100 includes: a first supporting portion 110 supporting the heater wire 210 and the sensor wire 310; a first heater electrode pad support 121 which supports the heater electrode pad 220; and a sensor electrode pad support 122 which supports the sensor electrode pad 320, wherein an air gap 101 is formed by removing the area except the first supporting portion 110, the heater electrode pad support 121, and the sensor electrode pad support 122.

A micro sensor according to another exemplary embodiment includes: a heater electrode 200 which includes a heater wire 210 wherein a plurality of first protrusions 211 are formed in the end portion thereof, and a first and a second electrode pads 220a and 220b which are connected to the both ends of the heater wire 210; and a sensor electrode 300 which includes a sensor wire 310 wherein a plurality of the second protrusions 311 are disposed between the first protrusions 211, and a sensor electrode pad 320 which is connected to the sensor wire 310; and a porous substrate 100 supporting the heater electrode 200 and the sensor electrode 300, wherein the porous substrate 100 includes: a first supporting portion 110 supporting the heater wire 210 and the sensor wire 310; a first heater electrode pad support 121a which supports the heater electrode pad 220a; a second heater electrode pad support 121b which supports the second heater electrode pad 220b; and a sensor electrode pad support 122 which supports the sensor electrode pad 320; and an air gap 101 formed outside of the first supporting portion 110.

At least a portion of the first heater electrode pad support 121a, the second heater electrode pad support 121b, and the sensor electrode pad support 122 is separated from each other by the air gap 101.

Example 2

Figure 4:
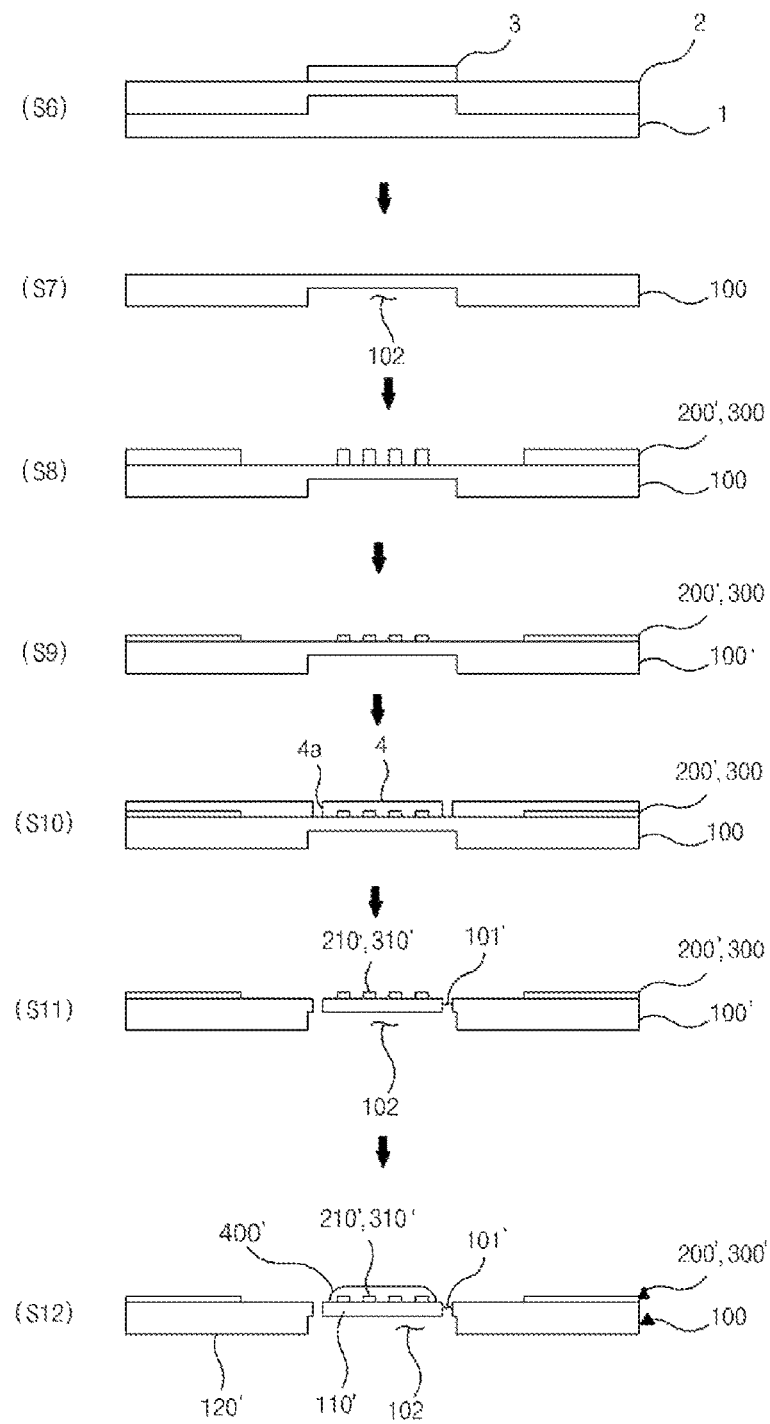

As illustrated in FIGS. 3 and 4, a method for manufacturing a micro sensor provided with the micro heater of the Example 2 includes the steps of: forming a heater electrode 200' and a sensor electrode 300' in the porous substrate 100' wherein an opening 102 is formed in the lower portion thereof; and forming an air gap 101' in the porous substrate 100', wherein the air gap 101' is communicating with the opening 102 and formed to surround the heater wire 210' of the heater electrode 200' and the sensor wire 310' of the sensor electrode 300'.

A method for manufacturing a micro sensor of the present exemplary embodiment includes the steps of S1 to S7 for forming the porous substrate 100' prior to the steps of S8 and S9 for forming the heater electrode 200' and the sensor electrode 300'.

The step for forming the porous substrate 100' may include the steps of: forming an aluminum oxide porous layer 2 through the oxidation of the aluminum substrate 1 (S4); forming a mask 3 on the aluminum oxide porous layer 2 (S5); thickening the aluminum oxide porous layer 2 through oxidation of the area of the aluminum substrate 1 except the mask 3 (S6); and forming the opening 102 through the etching of the other area in the aluminum substrate 1 except the area of the aluminum oxide porous layer 2 after removing the mask 3.

Prior to the step for forming the aluminum oxide porous layer 2 (S4), a step for preparing the bare aluminum substrate (S1); a step for forming the aluminum oxide porous layer 2 on the upper surface of the aluminum substrate 1, through oxidation of the upper surface of the aluminum substrate 1 for the first time (S2); and a step for etching the aluminum oxide porous layer 2 which had been already formed in the previous processes (S3) are further included.

Next, an aluminum oxide porous layer 2 is formed through oxidation of the aluminum substrate 1 for the second time. (S4)

Next, a mask 3 is formed in the upper middle portion of the aluminum oxide porous layer 2. (S5)

When oxidized with the mask 3, only the unmasked area is oxidized for the third time, but the masked area is not oxidized. (S6)

Thus, while the thickness of the masked portion of the aluminum oxide porous layer 2 is thin, the thickness of the unmasked portion of the aluminum oxide porous layer 2 becomes thick.

Next, the mask 3 is removed, and only the aluminum portion which is in the lower portion of the aluminum substrate 1 is etched away, thus a porous substrate 100' having an opening 102 is formed.

The heater electrode 200' and the sensor electrode 200' are formed on the upper surface of the porous substrate 100' manufactured in such a way. (S8, S9)

The steps for forming the heater electrode 200' and the sensor electrode 200' (S8, S9) include the steps of: forming the heater electrode 200' and the sensor electrode 200' for the first time (S8); and forming the heater electrode 200' and the sensor electrode 300' for the second time wherein the thickness thereof is being thinned (S9).

The heater electrode 200' includes a heater wire 210' and a heater electrode pad 220', and the sensor electrode 300' includes a sensor wire 310' and the sensor electrode pad 320'.

The heater wire 210' and the sensor wire 310' are disposed in the middle of the porous substrate 100'; and the heater electrode pad 220' and the sensor electrode pad 320' is disposed more outer side than the heater wire 210' and the sensor wire 310'.

Next, an air gap 101' is formed in the porous substrate 100'.

The step for forming the air gap 101' includes the steps of: forming a cover layer 4 wherein an imprinted air gap pattern 4a is formed corresponding to the portions wherein an air gap 101' is formed on the upper surface of the porous substrate 100', the heater electrode 200', and the sensor electrode 300' (S10); and etching the area exposed by the imprinted air gap pattern 4a in the porous substrate 100' (S11).

The step for forming the cover layer 4 (S10) may be implemented by a photoresist forming process.

After the etching step (S11), an air gap 101' which is penetrating along the vertical direction is formed in the porous substrate 100'.

The air gap 101', formed in this way, is communicating with the opening 102, and formed to surround the heater wire 210' and the sensor wire 310'. Due to this, the temperature can be increased to a high temperature using a low power since they have a small thermal capacity. Furthermore, it is thermally insulated along the vertical direction, and has an effect of longitudinal thermal insulation since the thickness of the heat radiating portion is reduced.

In addition, it is formed in a way that the outer most side of the opening 102 is disposed further towards the outer side than the outer most side of the air gap 101'.

After the step for forming the air gap 101', a step for forming the sensing material 400' on the porous substrate 100' covering the heater wire 210' and the sensor wire 310' (S12) may further be included.

The porous substrate 100' includes: a first supporting portion 110' which supports the heater wire 210' and the sensor wire 310'; and a second supporting portion 120' which supports the heater electrode pad 220' and the sensor electrode pad 320', wherein the sensing material 400' is formed in the location corresponding to the first supporting portion 110'.

The air gap 101' is formed outside of the first supporting portion 110'.

Figure 5:
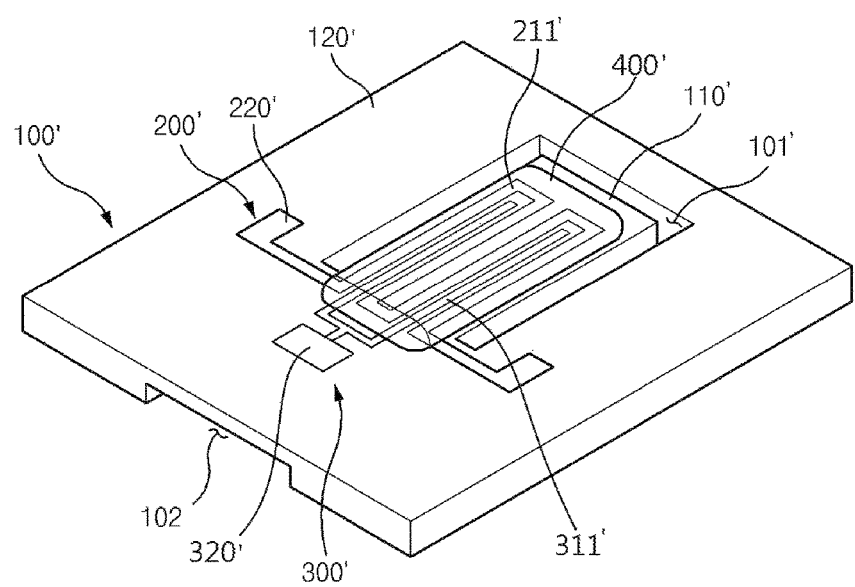
FIG. 5 is a perspective view of a micro sensor provided with a micro heater according to Example 2 of the present invention.

A micro sensor manufactured according to the above described method for manufacturing micro sensor, as illustrated in FIG. 5, includes: a porous substrate 100'; a sensor electrode 300' which is formed on the porous substrate 100' and includes a sensor wire 310' and a sensor electrode pad 320' being connected to the sensor wire 310'; and a heater electrode 200' which is formed on the porous substrate 100' and includes a heater electrode pad 220' and a heater wire 210' being connected to the heater electrode pad 220' and disposed more closely to the sensor wire 310' than the sensor electrode pad 320', wherein an air gap 101' which surrounds the heater wire 210' and the sensor wire 310' in the porous substrate 100'; and an opening 102 which is disposed in the lower portion of the heater wire 210' and communicating with the air gap 101' is formed in the lower portion of the porous substrate 100'.

The porous substrate 100' is formed with an aluminum material, and formed into a rectangular plate like shape.

The porous substrate 100' is formed with a porous layer. That is, the porous substrate 100' is formed with a porous material. Thus, a plurality of pores (not shown) with open upper end and lower end are penetratingly formed along the vertical direction in the porous substrate 100'

The porous substrate 100' can be formed through the oxidation of an aluminum substrate. Therefore, the porous substrate is an anodic aluminum oxide (AAO).

An opening 102 is formed along the forward and backward direction in the lower portion of the porous substrate 100'. The lower portions of the pores are communicating with the opening 102.

The sensor electrode 300' is formed on the upper surface of the porous substrate 100'.

Such sensor electrode 300' detects gases or humidity and the like.

The sensor electrode 300' includes a sensor wire 310' and a sensor electrode pad 320' which is connected to the sensor wire 310'.

The sensor wire 310' is disposed in the central portion of the porous substrate 100'.

A plurality of second protrusions 311' are formed at one side end of the sensor wire 310'. A plurality of second grooves are formed between the second protrusions 311' and the second protrusions 311' (that is, in between the second protrusions).

The sensor electrode pad 320' is formed to have a wider width than that of the sensor wire 310'. In addition, the sensor electrode pad 320' has a wider area than the sensor wire 310' when viewed from the top (in the plan view).

The heater electrode 200' is formed on the upper surface of the porous substrate 100. In this way, the thermal insulation effect is enhanced due to the pores (air holes) since the heater electrode 200' is formed on the porous layer.

The heater electrode 200' includes a heater electrode pad 220' and a heater wire 210' which is connected to the heater electrode pad 220' and disposed closer to the sensor wire 310' than the sensor electrode pad 320'.

The heater wire 210' is disposed in the central portion of the porous substrate 100'.

The sensor wire 310' and the heater wire 210' are disposed in the upper portion of the opening 102.

In the end portion of the heater wire 210', a plurality of the first protrusions 211' which are disposed inside the second groove, and a plurality of first grooves which is disposed inside the second protrusions 311' are formed. That is, the second protrusions 311' are disposed between the first protrusions 211'. The first protrusions 211' and the first grooves are plurally formed and alternately disposed. The first protrusions 211' and the first grooves are provided by the curvedly formed heater wire 210'.

On the whole, the heater wire 210' and the sensor wire 310' are formed to be a rectangular shape.

The heater electrode pad 220' is connected to both ends of the heat wire 210'. In this way, at least two each of the heater electrode pad 220' are formed.

The heater electrode pad 220' is formed to have a wider width than that of the heater wire 210'.

The air gap 101' is formed to surround the heater wire 210' and the sensor wire 310' along the circumference thereof in the porous substrate 100' of the porous substrate 100'.

The air gap 101' is formed to have a '∩' shape.

The air gap 101' is penetratingly formed along the vertical direction. Unlike this, the air gap 101' may be formed in a groove shape. The width of the air gap 101' is formed to be wider than that of the first protrusion 211' or the second protrusion 311'. The peak temperature of the radiating heat is getting higher as the width of the air gap 101' is getting wider.

Due to the air gap 101', a first supporting portion 110' which supports the heater wire 210' and the sensor wire 310'; and a second supporting portion 120' which supports the heater electrode pad 220' and the sensor electrode pad 320' are formed. That is, the air gap 101' is formed between the first supporting portion 110' and the second supporting portion 120'.

The first supporting portion 110' is formed to be a rectangular shape which is similar to the heater wire 210' and the sensor wire 310'; the first supporting portion 110' and the second supporting portion 120' are connected to each other at the area where the wires and pads are connected together; and the other portions are separated from each other due to the air gap 101'. Thus, the first supporting portion 110' and the second supporting portion 120' are connected at one point.

The entire portion of the first supporting portion 110' except the one side thereof is surrounded by the air gap 101'.

The first supporting portion 110' is formed to have a larger area than that of the heater wire 210' and the sensor wire 310'.

The width of the first supporting portion 110' is formed to be narrower than that of the opening 102. In addition, the opening 102 is formed in the end portion close to the first supporting portion 110' below the first supporting portion 110' and the second supporting portion 120'.

The thickness of the first supporting portion 110' is formed to be thinner than the average thickness of the second supporting portion 120'.

The opening 102 is communicating with the air gap 101'.

Air is disposed inside the air gap 101', so that the thermal insulation effect is enhanced, the thermal conductivity is decreased, and the thermal capacity can be reduced.

Further, a sensing material 400' covering the heater wire 210' and the sensor wire 310' is formed on the upper surface of the first supporting portion 110' of the porous substrate 100'.

The sensing material 400' is formed at the location corresponding to the first supporting portion 110'.

Hereinafter, the operation of an exemplary embodiment having the above described configuration will be explained.

In order to measure the gas concentration, first, a constant power is applied to the two heater electrode pads 220' of the heater electrode 200', and the area of the sensing material 400' of the center area of the sensor which is in contact therewith is heated to a constant temperature.

In this state, the change in the characteristics of the sensing material 400' generated when it is absorbed in or desorbed from the sensing material 400' corresponding to the concentration of the gas presented there around is measured using an external circuit by measuring the potential difference between the sensor electrode pads 320' which are electrically connected to the sensing material 400', and quantifying the electrical conductivity of the sensing material 400'.

In addition, for a more accurate measurement, concentration of an interested gas is measured after restoring the sensing material 400' to the initial state by forcibly removing the other residual gas or moisture already absorbed in the sensing material 400' through the heating thereof to a high temperature using the heater electrode 200'.

As described above, the micro heater and the micro sensor have an effect as follows.

The temperature can be increased to a high temperature using a low power since they have a small thermal capacity by forming an air gap which surrounds the heater wire and forming the heater wire in the porous substrate. In addition, the mechanical durability can be maintained since the portion of the heater wire is stably supported by the porous layer.

The thermal capacity can be further reduced by forming the area of the second supporting portion to be same as that of the heater electrode pad or to be larger than that of the heater electrode pad.

The porous layer can be easily formed since the porous substrate is formed with the aluminum oxide porous layer.

The heater wire can be more stably maintained since the area of the first supporting portion is formed to be larger than that of the heater wire.

When the heater wire and the sensor wire are not supported by a support, the sensing material is formed using dot method; however, the sensing material can be effectively formed by printing (process) since the heater wire and the sensor wire are supported by the first supporting portion.

An air gap, which surrounds the heater wire, is formed in the porous substrate; and an opening, which is disposed in the lower portion of the heater wire and communicating with the air gap, is formed in the lower portion of the porous substrate; thus, the thermal capacity can be reduced thereby, so the temperature can be increased to a high temperature with low power consumption. Furthermore, it is thermally insulated along the vertical direction, and has an effect of longitudinal thermal insulation since the thickness of the heat radiating portion is reduced. In addition, the mechanical durability can be maintained since the portion of the heater wire is stably supported by the porous layer.

It may have a more significant thermal isolation effect since the pores are penetratingly formed along the vertical direction in the porous substrate; and the pores are communicating with the opening.

As described above, although the present invention is described with reference to the preferred exemplary embodiments, those skilled in the art can implement the present invention through various modifications and alterations thereof without departing from the scope and spirit of the invention as disclosed in the accompanying claims.

What is claimed is:

1. A micro heater comprising:
   a porous substrate formed of an aluminum oxide porous layer;
   a heater electrode which is formed on said porous substrate and includes a heater wire and a heater electrode pad which is connected to said heater wire; and
   an air gap which surrounds said heater wire is formed in said porous substrate,
   wherein said air gap is formed by completely penetrating said porous substrate.

2. The micro heater according to claim 1,
   wherein a discoloration protection layer is formed on the upper side of said heater electrode and said discoloration protection layer comprises silicon dioxide or oxide series material.

3. A micro heater comprising:
a porous substrate; and
a heater electrode which is formed in said porous substrate and includes a heater wire and a heater electrode pad which is connected to said heater wire,
wherein a first supporting portion which supports said heater wire and a second supporting portion which supports said heater electrode pad are formed on said porous substrate, and an air gap is formed between said first supporting portion and said second supporting portion, and the shape of said second supporting portion is formed to be identical or similar to the shape of said heater electrode pad,
wherein said air gap is formed by completely penetrating said porous substrate.

4. A micro sensor comprising:
a porous substrate formed of an aluminum oxide porous layer;
a sensor electrode which is formed on said porous substrate and includes a sensor wire and a sensor electrode pad which is connected to said sensor wire;
a heater electrode which is formed on said porous substrate and includes a heater electrode pad, and a heater wire which is connected to said heater electrode pad and disposed closer to said sensor wire than said sensor electrode pad; and
an air gap which surrounds said heater wire and said sensor wire is formed in said porous substrate, wherein said air gap is formed by completely penetrating said porous substrate.

5. The micro sensor according to claim 4, wherein a sensing material covering said heater wire and said sensor wire is further included.

6. A micro sensor comprising:
a heater electrode which includes a heater wire wherein a plurality of first protrusions are formed in the end portion thereof, and a heater electrode pad being connected to said heater wire;
a sensor electrode which includes a sensor wire wherein a plurality of second protrusions disposed between said first protrusions, and a sensor electrode pad being connected to said sensor wire; and
an aluminum oxide porous layer which supports said heater electrode and said sensor electrode; and
an air gap formed between said heater electrode pad and said sensor electrode pad by removing a portion of said aluminum oxide porous layer, wherein said air gap is formed by completely penetrating said aluminum oxide porous layer.

7. The micro sensor according to claim 6,
wherein said aluminum oxide porous layer includes a first supporting portion which supports said heater wire and said sensor wire, wherein said air gap is formed outside of said first supporting portion.

8. The micro sensor according to claim 7,
wherein a sensing material is additionally formed in the location corresponding to said first supporting portion.

9. The micro sensor according to claim 6,
wherein said aluminum oxide porous layer includes:
a first supporting portion which supports said heater wire and said sensor wire;
a heater electrode pad support which supports heater electrode pad and formed to have a same outline of said heater electrode pad but having a wider width than that of said heater electrode pad; and
a sensor electrode pad support which supports said sensor electrode pad and formed to have a same outline of said sensor electrode pad but having a wider width than that of said sensor electrode pad.

10. The micro sensor according to claim 6,
wherein a discoloration protection layer is formed on the upper side of said heater electrode or said sensor electrode, and said discoloration protection layer comprises silicon dioxide or oxide series material.

11. A micro sensor comprising:
a porous substrate;
a sensor electrode which is formed on said porous substrate and includes a sensor wire and a sensor electrode pad which is connected to said sensor wire; and
a heater electrode which is formed on said porous substrate and includes a heater wire and heater electrode pad which is connected to said heater wire,
wherein said porous substrate includes:
a sensor electrode pad support which supports said sensor electrode pad; and
a heater electrode pad support which supports said heater electrode pad; and
an air gap is formed between said heater electrode pad support and said sensor electrode pad support, wherein said air gap is formed by completely penetrating said porous substrate.

12. A micro sensor comprising:
a porous substrate;
a sensor electrode which is formed on said porous substrate and includes a sensor wire, and a sensor electrode pad which is connected to said sensor wire; and
a heater electrode which is formed on said porous substrate and includes a heater wire, and a heater electrode pad which is connected to said heater wire,
wherein said porous substrate includes:
a first supporting portion which supports said heater wire and said sensor wire;
a heater electrode pad support which supports said heater electrode pad;
a sensor electrode pad support which supports said sensor electrode pad; and
an air gap is formed by removing all portions of said porous substrate except said first supporting portion, said heater electrode pad support, and said sensor electrode pad support, wherein said air gap is formed by completely penetrating said porous substrate.

13. A micro sensor comprising:
a heater electrode which includes a heater wire wherein a plurality of first protrusions are formed in the end portion thereof, and a first and a second heater electrode pads which are connected to both sides of said heater wire;
a sensor electrode which includes a sensor wire wherein a plurality of second protrusions are disposed between said first protrusions, and a sensor electrode pad which is connected to said sensor wire; and
a porous substrate which supports said heater electrode and said sensor electrode,
wherein said porous substrate includes:
a first supporting portion supporting said heater wire and said sensor wire;
a first heater electrode pad support which supports said first heater electrode pad;
a second heater electrode pad support which supports said second heater electrode pad;
a sensor electrode pad support which supports said sensor electrode pad; and an air gap which is formed on an outer side of said first supporting portion, wherein said air gap is formed by completely penetrating said porous substrate.

14. The micro sensor according to claim 13, wherein at least a portion of said first heater electrode pad support, said second heater electrode pad support, and said sensor electrode pad support is separated from each other by said air gap.

15. A micro heater comprising:
a porous substrate formed of an aluminum oxide porous layer;
a heater electrode which is formed on said porous substrate and includes a heater wire and a heater electrode pad which is connected to said heater wire;
an air gap which surrounds said heater wire is formed in said porous substrate, wherein said air gap is formed by completely penetrating said porous substrate; and
an opening, which is disposed in the lower portion of said heater wire and communicating with said air gap, is formed in the lower portion of said porous substrate.

16. The micro heater according to claim 15, wherein a plurality of pores are penetratingly formed along the vertical direction in said porous substrate; and said pores are communicating with said opening.

17. A micro sensor comprising:
a porous substrate formed of an aluminum oxide porous layer;
a sensor electrode which is formed on said porous substrate and includes a sensor wire and a sensor electrode pad which is connected to said sensor wire;
a heater electrode which is formed on said porous substrate and includes a heater electrode pad, and a heater wire which is connected to said heater electrode pad and disposed closer to said sensor wire than said sensor electrode pad;
an air gap, which surrounds said heater wire and said sensor wire, is formed in said porous substrate; and
an opening, which is disposed in the lower portion of said heater wire and communicating with said air gap, is formed in the lower portion of said porous substrate,
wherein said air gap is formed by completely penetrating said porous substrate.

18. The micro sensor according to claim 17, wherein a sensing material is formed in said porous substrate in a way that said heater wire and said sensor wire are covered thereby.

* * * * *